US009808592B2

(12) United States Patent
Melsheimer et al.

(10) Patent No.: US 9,808,592 B2
(45) Date of Patent: Nov. 7, 2017

(54) NEBULIZING CATHETER FOR BRONCHIAL THERAPY

(71) Applicant: Cook Medical Technologies LLC, Bloomington, IN (US)

(72) Inventors: Jeffry S. Melsheimer, Springville, IN (US); Frank J. Fischer, Jr., Bloomington, IN (US)

(73) Assignee: Muffin Incorporated, West Lafayette, IN (US)

( * ) Notice: Subject to any disclaimer, the term of this patent is extended or adjusted under 35 U.S.C. 154(b) by 208 days.

(21) Appl. No.: 13/939,411

(22) Filed: Jul. 11, 2013

(65) Prior Publication Data
US 2014/0018616 A1 Jan. 16, 2014

Related U.S. Application Data

(60) Provisional application No. 61/671,237, filed on Jul. 13, 2012.

(51) Int. Cl.
A61M 16/04 (2006.01)
A61M 11/00 (2006.01)
(Continued)

(52) U.S. Cl.
CPC ......... A61M 16/04 (2013.01); A61B 1/00091 (2013.01); A61B 1/018 (2013.01); A61B 1/05 (2013.01); A61B 1/2676 (2013.01); A61M 11/005 (2013.01); A61M 16/0057 (2013.01); A61M 16/0463 (2013.01);
(Continued)

(58) Field of Classification Search
CPC .............. A61M 16/04; A61M 16/0463; A61M 16/0488; A61M 16/0057; A61M 16/208; A61M 11/005; A61M 2205/502; A61M 2205/8206; A61M 11/001; A61M 11/042; A61M 11/06; A61M 15/00; A61M 15/0083; A61M 15/0085; A61M 15/009; A61M 15/025; A61M 15/06; A61M 16/00; A61M 16/14; A61M 2016/0024; A61M 2016/0027; A61M 2025/0035; A61M 2025/0036; A61M 2025/0037; A61M 2025/0039; A61M 2025/004; A61M 2025/0073; A61M 2205/0266; A61M 2205/3561; A61M 2205/3569; A61M 2205/3592; A61M 2205/3653; A61M 2205/50; A61M 2205/8256; A61M 2209/10; A61M 25/0009; A61M 25/003; A61M 25/0068; A61M 25/0071;
(Continued)

(56) References Cited

U.S. PATENT DOCUMENTS 4,961,885 A 10/1990 Avrahami et al.
5,031,613 A 7/1991 Smith et al.
(Continued)

Primary Examiner — Annette Dixon
(74) Attorney, Agent, or Firm — Woodard Emhardt Moriarty McNett & Henry LLP

(57) ABSTRACT

A nebulizing catheter for bronchial therapy includes a catheter having a sheath defining an interior space and an open tip. A nebulizer is positioned in the interior space and located adjacent the open tip. The nebulizer includes a piezoelectric device. A liquid mixture is provided and placed in flow communication with the piezoelectric device for nebulizing a portion of that liquid mixture into small droplets for use in the bronchial therapy.

24 Claims,

(51) Int. Cl.
  *A61M 16/00* (2006.01)
  *A61M 16/20* (2006.01)
  *A61B 1/018* (2006.01)
  *A61B 1/267* (2006.01)
  *A61B 1/00* (2006.01)
  *A61B 1/05* (2006.01)
  *A61B 1/005* (2006.01)

(52) U.S. Cl.
  CPC ...... *A61M 16/0488* (2013.01); *A61M 16/208* (2013.01); *A61B 1/005* (2013.01); *A61M 2205/502* (2013.01); *A61M 2205/8206* (2013.01)

(58) Field of Classification Search
  CPC ....... A61B 1/00091; A61B 1/05; A61B 1/018; A61B 1/2676; A61B 1/005; A61B 90/70
  USPC ............ 128/200.11, 207.14, 200.14, 200.16; 604/508, 510, 526, 528, 529, 530
  See application file for complete search history.

(56) References Cited

U.S. PATENT DOCUMENTS

| | | |
|---|---|---|
| 6,357,671 B1 | 3/2002 | Cewers |
| 7,472,705 B2 | 1/2009 | Baran |
| 7,571,722 B2 | 8/2009 | Wuttke et al. |
| 7,588,322 B2* | 9/2009 | Ohnishi ............... B41J 2/14209 347/68 |
| 7,810,742 B2 | 10/2010 | Levi |
| 2004/0084049 A1* | 5/2004 | Baran ...................... 128/207.14 |
| 2007/0157931 A1* | 7/2007 | Parker et al. ............ 128/204.23 |
| 2007/0267031 A1* | 11/2007 | Hon ...................... A24F 47/008 131/273 |
| 2008/0078383 A1 | 4/2008 | Richards et al. |
| 2008/0283051 A1 | 11/2008 | Faram |

* cited by examiner

NEBULIZING CATHETER FOR BRONCHIAL THERAPY

CROSS REFERENCE TO RELATED APPLICATION

This application claims the benefit of U.S. Provisional Application Ser. No. 61/671,237 filed Jul. 13, 2012 which is hereby incorporated by reference.

BACKGROUND

The treatment of respiratory ailments often includes the delivery of medications by the use of a nebulizer. Typically a nebulizer works by using an air compressor and a nebulizer cup in order to turn medication into a vapor mist or fog for the patient to inhale. A variety of nebulizer constructions are known to exist and the vapor mist or fog of medication may be inhaled passively (from the surrounding atmosphere) or inhaled actively by the use of an inhaler. Each inhalation approach includes certain drawbacks which offer opportunities for design improvements.

Figure 4:
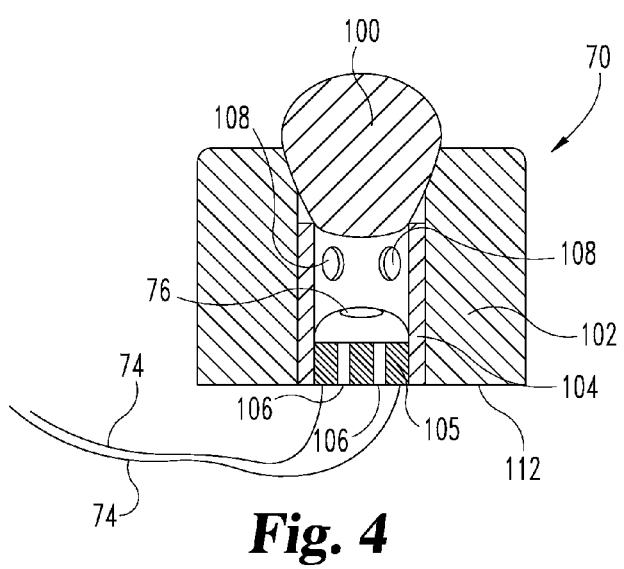

In the case of passive inhaling, the nebulizing process dilutes the medication as it diffuses from the nebulizer machine into the surrounding atmosphere. As a result of this dilution, a more concentrated dose of medicine is required in order to achieve the desired treatment. This process, as described, may be "acceptable" for certain medicines and certain treatments, at least from a cost perspective when the medicine is a relatively low cost item. However, when the nebulizing procedure is used for cell therapy, the modified cells are too precious to waste. Even if we discount the loss of modified cells to the surrounding atmosphere, there are further losses associated with the act of inhaling, whether active or passive inhaling. Active inhaling causes some of the nebulized cells to be absorbed by the mouth and throat tissues before reaching the site needing or targeted for the therapy.

In addition to the fact that the modified cells are too precious to waste, the therapy is more effective when the modified cells are delivered directly to the localized area, including the patient site which will primarily benefit from the treatment. The typical delivery process for respiratory treatment, consistent with the prior art, consists of atomizing the modified cells and then allowing normal respiration to distribute the cells somewhat uniformly to the entire lung.

As noted, modified cells are too precious to waste. Further, the therapy is more effective when the modified cells are directed in a more focused or targeted manner directly to the area or patient site which will benefit from the treatment. When the delivery of nebulized modified cells, via normal respiration, extends to the entire lung, some other areas or portions of the lung receive the modified cells which are not part of the area or location targeted for treatment. Since these "other" areas of the lung are not intended for treatment and thus would understandably not benefit from receiving the modified cells, a portion of the modified cells which are delivered to the lung are "wasted". The disclosed embodiment addresses this prior art issue by providing a nebulizing catheter which includes the use of a bronchoscope for catheter delivery and for positioning the dispensing tip of the catheter at or near the selected treatment site within a lung of the patient or subject.

In the context of the present disclosure, other prior art methods of fog-generation for respiratory treatment create droplets larger than those formed by nebulizing. The result of having larger droplets means that uptake by the smallest bronchioles and alveoli will be inhibited and the intended treatment less effective. In part, this is why nebulizing is a preferred approach for cell therapy, using modified cells. However, the prior art forms of nebulizing and the prior art methods of treatment are improved upon by the disclosed embodiment and the associated method.

Nebulizing results in the creation of smaller-sized droplets, and thus the reference to "fog", as these smaller-sized droplets are of "mist" size and carried by an air flow. These smaller droplets are able to reach farther into smaller passageways of the lungs before uptake. Because the nebulized droplets are smaller, they exhibit better uptake via cell-wall transfer. A result of this is that small dosages of the modified-cell solution (referred to herein as a "liquid mixture") can be effective when applied directly to the treatment area or site.

SUMMARY

A nebulizing catheter for bronchial therapy includes a catheter having a sheath defining an interior space and an open tip. A nebulizer is positioned in the interior space and located adjacent the open tip. The nebulizer includes a piezoelectric device. A liquid mixture is provided and placed in flow communication with the piezoelectric device for nebulizing a portion of that liquid mixture into small droplets for use in the bronchial therapy.

A bronchial therapy device includes a supply of air, a handle connected to the supply of air and a nebulizing catheter which is connected to the handle. The nebulizing catheter includes a catheter having a sheath defining an interior space and an open tip. A nebulizer is positioned in the interior space and located adjacent the open tip. The nebulizer includes a piezoelectric device. A liquid mixture is provided and placed in flow communication with the piezoelectric device for nebulizing a portion of that liquid mixture into small droplets for use in the bronchial therapy.

A method of providing bronchial therapy treatment to a patient site includes the steps of first providing a handle, providing a nebulizing catheter which is operatively connected to the handle and providing the nebulizing catheter with a nebulizer which includes a piezoelectric device. One of the steps being performed is to connect the handle to a supply of air. A next step is to position the tip of the nebulizing catheter at the patient site. Thereafter, the nebulizing catheter is supplied with a liquid mixture and this liquid mixture is positioned near the nebulizer. Once all of the component parts and materials are in place, the piezoelectric device is energized and converts a portion of the liquid mixture into small droplets which are suitable for bronchial therapy treatment.

BRIEF DESCRIPTION OF THE DRAWINGS

FIG. 1 is a diagrammatic, perspective view of a bronchial therapy device according to the present disclosure.

FIG. 1A is an enlarged view of a portion of the FIG. 1 illustration showing a nebulizing catheter tip positioned in a lung of a patient.

FIG. 2 is an enlarged perspective view of the tip portion of a nebulizing catheter which comprises one portion of the FIG. 1 bronchial therapy device.

FIG. 2A is an enlarged detail of the FIG. 2 illustration showing an alternative structure for liquid mixture delivery.

FIG. 3 is a front elevational view, in full section, of a liquid mixture reservoir which comprises one portion of the FIG. 2 nebulizing catheter.

FIG. 4 is a front elevational view, in full section, of a nebulizer and surrounding structure comprising a portion of the FIG. 2 nebulizing catheter.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 1:
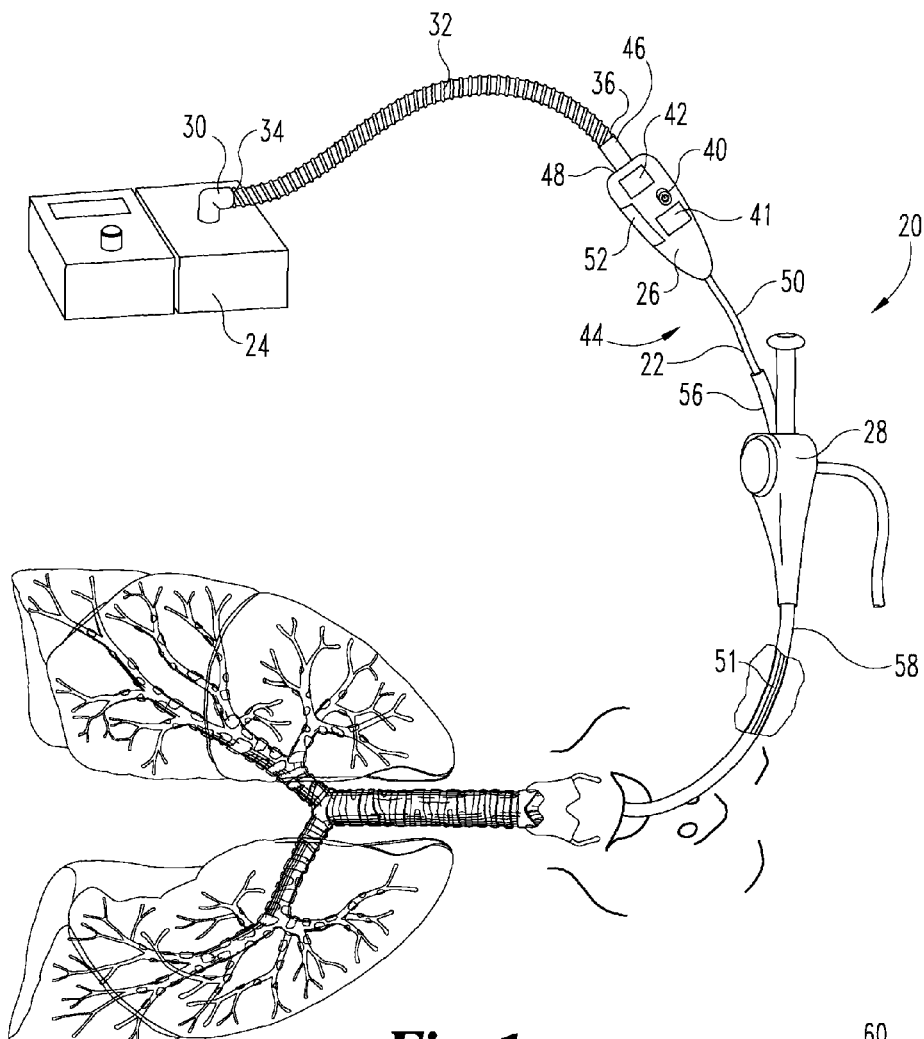

Referring to FIG. 1, a diagrammatic illustration of a bronchial therapy device 20 is provided which is consistent with the disclosed embodiment. Although much of the inventive focus herein is directed to the nebulizing catheter 22, all of the disclosed components and subassemblies are important to the totality of the FIG. 1 bronchial therapy device 20 and to an understanding of bronchial therapy device 20 and its method of use. With continued reference to FIG. 1, device 20 further includes a continuous positive airway pressure (CPAP) unit 24, a handle 26 for and associated with the nebulizing catheter 22 and a flexible bronchoscope 28.

A CPAP unit, such as unit 24, is a ventilation device which generates a gentle stream of air. One of the intended uses for this gentle stream of air is to direct it into the nose and/or the mouth of a subject or patient during sleep in order to keep the airway open. This type of device creates positive pressure ventilation for subjects who are breathing spontaneously in order to keep the soft palate from collapsing into the airway and thus increase oxygenation and reduce the work of breathing. Important to the disclosed embodiment of FIG. 1 is that current CPAP technology is able to be used in order to generate an inward flow of air at a programmable level of pressure, and document this flow of air which is used as part of the intended bronchial therapy.

CPAP unit 24 which is responsible for the supply of air includes an air outlet port 30 from which the gentle stream of air flows when CPAP unit 24 is operated. A flexible, hollow air flow conduit 32 (i.e. hose) is connected at one end 34 to CPAP unit 24. The opposite end 36 is connected to handle 26. Ideally, the connections at ends 34 and 36 are tight, secure and leak-free so that the full volume of air from CPAP unit 24 is directed to and reaches handle 26. The actual connection or fitting between flow conduit 32 and handle 26 can be a pressure fitting, a threaded fitting, over-molded or a quick-connect fitting, including a bayonet-type fitting, to mention a few of the suitable options. Similar structures may be used for the connection of flow conduit 32 to CPAP unit 24.

The handle 26 (see FIG. 2) is considered an important and cooperating part of the device which includes nebulizing catheter 22, since handle 26 includes a battery which is used to provide the electric energy for a piezoelectric device 76 which is positioned in the distal end 38 of the nebulizing catheter 22. Handle 26 also includes an ON/OFF switch 40, a control pad 41 and a status display window 42. Handle 26 also includes wave generator circuitry which generates the distinct electrical signal which is preferred for nebulizing the selected medicant solution. This electrical signal is sent to the piezoelectric device adjacent the distal tip 62. The control pad 41 enables the nebulizing catheter 22 to be selectively actuated. Since portions of the handle 26 have a direct effect on the components of the nebulizing catheter 22 which are found in distal end 38, it is logical to treat the handle 26 in combination with the nebulizing catheter 22 as a "nebulizing device" 44 and this terminology and convention is being adopted for the present disclosure. The need to adopt a specific agreed terminology such as "nebulizing device" 44 is due in part to the physical positioning of the flexible bronchoscope 28 which is downstream from the handle 26 and which receives a portion of the nebulizing catheter 22. Accordingly, the two (2) components (handle 26 and nebulizing catheter 22) which are cooperatively connected together comprise nebulizing device 44.

Nebulizing catheter 22 extends from its point of connection to or with handle 26 to its opposite distal end which includes open tip 62. For use in describing what is illustrated in the drawings, nebulizing catheter 22 includes three (3) sections or portions. These three (3) portions of catheter 22 include portion 50, portion 51 and portion 60. Portion 50 extends between handle 26 and port 56 of bronchoscope 28. Portion 51 extends through bronchoscope 28 and its flexible tube 58 until the nebulizing portion 60 is reached. The nebulizing portion 60 is roughly defined as the distal portion of catheter 22 which includes many of the nebulizing components, collectively referred to as nebulizer 70. The entirety of nebulizing catheter 22 provides a means for the passage of the electrical wiring from a power source in the handle 26 to the nebulizer 70 and for the flow of air from CPAP unit 24. Each portion 50, 51 and 60 has an outside diameter size of approximately between 3.6 mm and 4.0 mm. This diameter size is important for receipt of the catheter 22 by bronchoscope 28 and by the selected channel of flexible tube 58.

Handle 26 includes a flow connection port 46 adjacent the proximal end 48 and receives catheter portion 50. Port 46 is constructed and arranged with a suitable fitting or other mechanical structure for connecting to or with the opposite end 36 of flow conduit 32. Handle 26 further includes a removable battery cover 52 for the battery (or batteries) (not illustrated) which are connected in the interior of handle housing 54. As noted above, each catheter portion 50, 51 and 60 has an outside diameter of approximately between 3.6 mm and 4.0 mm. This size is important due to the channel sizes of the bronchoscope 28 and is important for the overall passage of the nebulizing catheter 22 as well as the catheter tip 62 which is to be located at or near the treatment site within the lung of a patient. The catheter portion 50 is received by handle 26 and is inserted into a connection port 56 of the flexible bronchoscope 28. While the approximate 4.0 mm size is maintained for most of catheter 22, open tip 62 includes a slight taper and thus a slightly smaller outside diameter.

Connection port 56 is often used for sectioning or instrumentation, but as a point of entry for a flow conduit or catheter, the passage of media can be in either direction. In the case of bronchial therapy device 20, catheter portion 50 is inserted into port 56 and catheter portion 51 extends from port 56 through one (1) of the channels of flexible tube 58 of flexible bronchoscope 28. The distal end of catheter portion 51 is integral with nebulizing portion 60. The continuous catheter 22 which includes portions 50, 51 and 60 together comprise nebulizing catheter 22. While the nebulizing catheter 22 is a continuous length of tubing, the reference to nebulizing portion 60 is based on where the majority of the nebulizing components are housed, and this portion generally corresponds with distal end 38.

Flexible bronchoscope 28 has a separate and stand-alone unit as a construction which is considered as being generally typical or standard of prior art constructions. However, the incorporation of this flexible bronchoscope into the disclosed bronchial therapy device 20 is novel and unobvious. Positioning flexible bronchoscope 28 downstream from handle 26 and providing a means for receiving catheter portion 51 of nebulizing catheter 22 are novel and unobvious features. This unique combination and arrangement creates a novel and unobvious device 20 and a novel and unobvious method of using device 20.

A part of the flexible style is a visualization system which may include fiber optics and/or a charge coupled device (CCD) or a complementary metal oxide semiconductor (CMOS) camera. An image is transmitted from the tip of the instrument to an eyepiece or video camera at the opposite end. Cables connected to a lever at the hand piece enable the tip of the instrument to be oriented and the practitioner is able to navigate the instrument into individual lobe or segment bronchi.

The flexible tube 58 of flexible bronchoscope 28 is divided into three (3) channels. The first channel is a fiber optic channel which delivers illumination to the distal end or tip of the flexible tube 58. The second channel includes an optic system which allows the physician to view inside the lungs. The third channel allows the through passage of catheter portion 51 which is part of the nebulizing catheter 22, and allows the passage of the distal end 38 (i.e. portion 60) of nebulizing catheter 22.

Figure 1A:
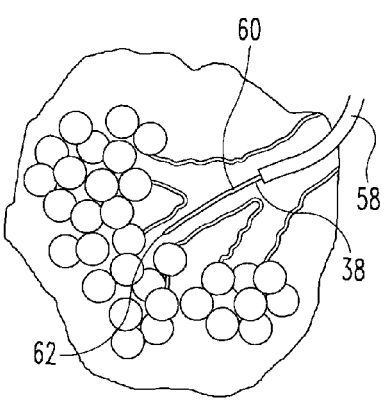

As diagrammatically illustrated in FIGS. 1 and 1A, flexible tube 58 is inserted into the patient's (or subject's) mouth and extends through the airway and into the lungs. For the disclosed embodiment, the flexible bronchoscope 28 is used to guide the distal tip 62 of nebulizing catheter 22 to the treatment site within the lungs. In this way, when a nebulizing "fog" of the modified cells is produced, those modified cells are delivered directly to the treatment site. The modified cells are not wasted by having the fog dispersed to other portions of the lungs which are not targeted for therapy. The FIG. 1A illustration shows the distal tip 62 of nebulizing catheter 22 at its treatment site position within a lung.

Direct application of the nebulized cells according to the present disclosure is a more efficient method and treatment because those cells which are inhaled get absorbed by the mouth and throat tissues before reaching the site needing the therapy. Nebulizing creates smaller-sized droplets which can reach further into smaller passageways before uptake. Nebulized droplets are smaller and therefore exhibit better uptake via cell-wall transfer. Smaller dosages of modified-cells can be effective when applied directly to the treatment area. The nebulizing catheter may indwell after initial treatment until it is determined whether or not additional treatments are desired.

Figure 2:
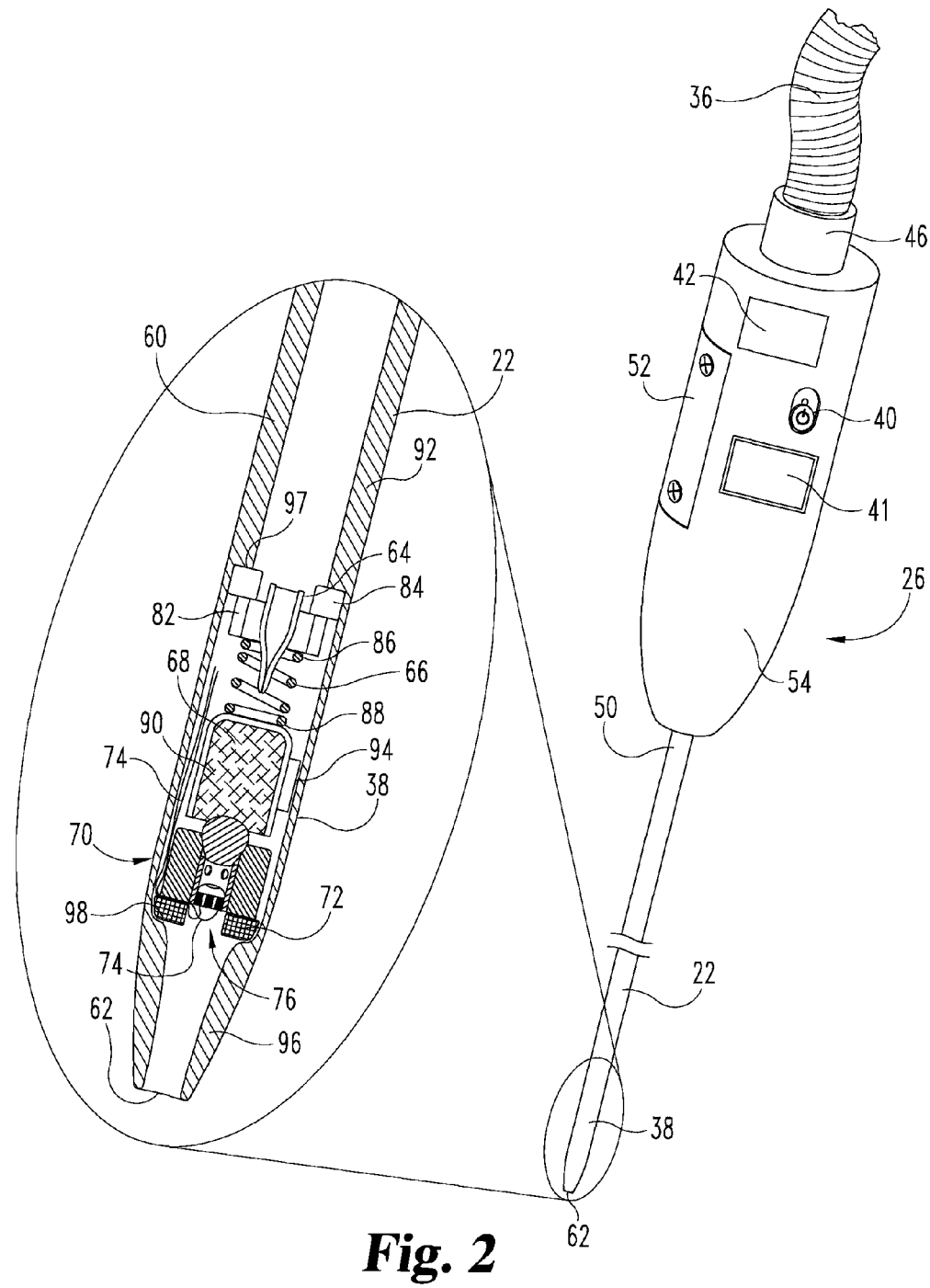

Referring now to FIG. 2, additional component parts of the nebulizing catheter 22 are illustrated. As noted thus far, the nebulizing device 44 includes the combination of handle 26 and nebulizing catheter 22. The nebulizing catheter 22 includes catheter portions 50 and 51 in combination with nebulizing portion 60. Nebulizing portion 60 includes distal end 38 and the open distal tip 62 and the additional component parts now being described are assembled into and housed by distal end 38. These additional component parts include a one-way valve 64, spring 66, reservoir 68, nebulizer 70 and mounting ring 72. Also included is the electrical wiring 74 from the handle 26 for electrical energy connection from the battery (or batteries) assembled into the handle 26 to the piezoelectric device 76 which can be thought of for the exemplary embodiment as being an ultrasonic transducer. Piezoelectric device 76 is a part of the nebulizer 70. Nebulizer 70 is positioned adjacent open tip 62.

Valve 64 is a silicone member having a duck-bill construction with an open proximal end 78 and a normally-closed distal end 80. The valve 64 is held by alignment ring 82 which seats against annular-ring spacer 84. Spring 66 is a coil spring which abuts against ring 82 at one end 86 and abuts against reservoir 68 at the opposite end 88. Valve 64 is constructed and arranged so as to easily open in only one flow direction upon receipt of air flow from the CPAP unit 24. When the air stops flowing or when the flow of air reaches a very low level, insufficient to open valve 64, the distal end of valve 64 which includes the two (2) closing flaps, remains closed. At this point, any reverse flow upstream away from the location of the nebulizer 70 is prevented from flowing through valve 64 or flowing past the location of valve 64 due to its duck-bill construction, the normally-closed condition of distal end 80 and the additional surrounding components and structures which cooperate with valve 64 to block any upstream flow.

Figure 3:
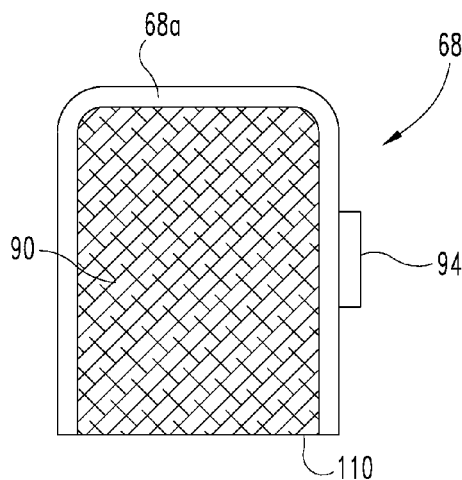

Reservoir 68 (see FIG. 3) includes a fine mesh 90 which is held within reservoir wall 68a. The fine mesh 90 is constructed and arranged for capturing and holding a liquid or liquid mixture for ultimately nebulizing into a fog for treatment. Included as a part of this liquid or liquid mixture are the modified cells. The construction and arrangement of the fine mesh 90 retains the liquid-cell mixture without running, dripping or other forms of leakage. The fine mesh 90 may be a type of batting of a polyester material or of similar synthetic materials. A liquid or liquid mixture containing the modified cells for the desired therapy is loaded into reservoir 68 by means of a hypodermic needle syringe, according to one (1) embodiment.

In the exemplary embodiment, the components are sealed into nebulizing catheter 22 as illustrated and described. Therefore, one option for filling the reservoir 68 is to introduce an injection (i.e., filling) hypodermic needle (not illustrated) through sheath 92 at a predesignated location or area generally adjacent to reservoir 68. The hypodermic needle is used to dispense the medicant solution into the reservoir. Selecting a compliant material for sheath 92, such as an elastomeric polymer, allows the sheath wall to be self-sealing at least to some degree. Any minor opening or perforation which might remain would be inconsequential.

The spring 66 is compressed slightly so as to spring bias the fine mesh 90 portion of the reservoir 68 up against the porous plug 100. The abutment stack of component parts extends between two (2) ledges 97 and 98 which are formed on the interior of the catheter sheath 92. Alignment ring 82 abuts up against spacer 84 which abuts up against proximal ledge 97. Mounting ring 72 abuts up against distal ledge 98 and porous body 102 abuts up against mounting ring 72. This spring-biased construction facilitates a type of capillary action for the flow of liquid from the reservoir 68 to the porous plug 100.

Figure 2A:
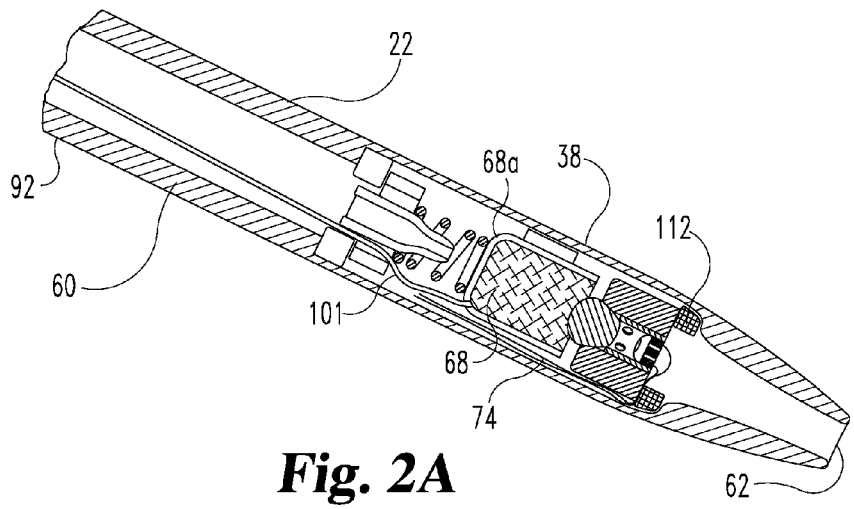

With regard to the loading of modified cells (as part of a liquid mixture) into the reservoir, a second embodiment is diagrammatically illustrated in FIG. 2A. As is illustrated, a small tube 101 extends through the interior space of sheath 92 and connects through the outer wall 68a of the reservoir so as to establish liquid flow communication with fine mesh 90. The small tube 101 is used as a liquid lumen and is connected to the handle 26 or at least communicates with the handle 26 such that a liquid mixture, including modified cells, is able to be introduced into the liquid lumen 101 at or near the location of the handle 26. By connecting the lumen 101 to the handle 26, the lumen may be filled, re-filled and/or pre-filled with the working fluid (i.e. the liquid mixture containing the modified cells, according to one embodiment). In other embodiments, the working fluid may have a different composition and/or a different intended use. In other embodiments, the lumen 101 may be used in other ways such as providing the capability to be aspirated/pressurized.

The electrical wiring 74 runs down one (1) side of the reservoir 68. In order to position reservoir 68 generally centrally within the interior space of catheter sheath 92, a spacer 94 is used on the opposite side of the reservoir between the reservoir 68 and the sheath 92 wall. The open tip 62 of distal end 38 of sheath 92 (i.e. a part of the nebulizing portion 60) is tapered, a shape which results from heat shaping of the material used for sheath 92. A thicker sheath section 96 is adjacent mounting ring 72 and provides ledge 98. The mounting ring 72 is positioned between ledge 98 and nebulizer 70.

Referring now to FIG. 4, the components, construction and details of nebulizer 70 are illustrated. Included as a part of nebulizer 70 are porous plug 100, porous body 102 and sleeve 104. Sleeve 104 should be substantially rigid and electrically non-conducting. In the exemplary embodiment sleeve 104 is made out of a ceramic material. The piezoelectric device (an ultrasonic transducer) 76 is positioned in the ceramic sleeve 104. The ultrasonic transducer 76 which corresponds to the piezoelectric device in the exemplary embodiment is suspended in the interior of the cavity defined by ceramic sleeve 104. This suspension may be achieved by the wiring "legs" associated with the ultrasonic transducer. Positioned within the distal end of ceramic sleeve 104 is a press-fit holder 105 which defines perforated outlets for the nebulized fog, identified herein as outlet passages 106. Holder 105 may be fabricated out of a ceramic material similar to that used for sleeve 104. Holder 105 helps to maintain the position and location of ultrasonic transducer 76.

The electrical wiring 74 which comes from the handle 26 is shown as being connected to the piezoelectric device 76. The ceramic sleeve 104 defines apertures 108 for the passage and mixing of air and liquid into the vicinity of the piezoelectric device 76. The liquid mixture which begins in reservoir 68 and migrates to porous plug 100 and therefore to porous body 102 is in air-flow communication with piezoelectric device 76. This air and liquid mixture is acted on by the ultrasonic vibrations or waves which are produced by the piezoelectric device 76 thereby converting this liquid mixture into a fog composition of extremely small droplets which includes the modified cells. The produced fog represents an expanded volume which seeks an exit path of least resistance and this exit path of least resistance is provided by outlet passages 106.

The nebulizer 70 is described as including a piezoelectric device 76 which in the exemplary embodiment includes at least an ultrasonic transducer. The phrase "piezoelectric device" could also be used to broadly cover a variety of components and component combinations which cooperate with the ultrasonic transducer in some capacity, such as the referenced wave generator. The fluid reservoir either contains the modified-cell solution (i.e. the liquid mixture) or is able to be supplied with the modified-cell solution, such as via a lumen 101. Thousands of laser-drilled holes form micro-perforations (i.e. a mesh) in the transducer. When energized, the vibrations imparted by the ultrasonic transducer nebulize the solution which directly "fogs" the tissue of the selected treatment site as the generated fog exits from the distal tip 62.

The air flow continues as long as the CPAP unit 24 operates. The amount or volume of liquid which is present when the procedure begins is based on what was initially injected into reservoir 68. By placing the porous plug 100 directly up against the open end 110 of reservoir 68, and actually into the fine mesh 90, the liquid mixture which typically saturates the fine mesh 90 of the reservoir migrates from the fine mesh 90 to the porous plug 100, similar to liquid flow due to capillary action. From the porous plug 100 the liquid mixture flows into the surrounding porous body 102, essentially by the same flow principal. The flow of air through the nebulizing catheter 22 is ultimately directed at the porous body 102. The force of the airflow, even though at an extremely low pressure, is sufficient to pass through the porous body 102 and porous plug 100, and through the cavity of sleeve 104 such that the generated fog is transported via this air flow, out through passages 106 and distal tip 62, and made available to the adjacent tissue. The mounting ring 72 closes off the distal end or face 112 of the porous body 102 thereby helping to ensure that the path of least resistance for the airflow (and the liquid mixture being carried) is through apertures 108. As the liquid concentration in the porous body 102 is reduced or lowered, the higher liquid concentration in the reservoir 68 continually replenishes the diminishing level in porous body 102 and in porous plug 100 due to capillary action, until the reservoir is depleted or the therapy is discontinued. This procedure is able to continue until most all of the liquid mixture which was injected into the reservoir has been converted into fog or until the treatment at the selected site has been concluded. Re-filling the reservoir remains an option even during treatment. Injecting more of the liquid mixture into the reservoir allows the therapy process/procedure to continue. The construction and arrangement of nebulizing catheter 22, noting its small size and flexible construction, allows it to remain in the patient (i.e. indwell) after initial treatment until it is determined whether or not additional treatments are desired.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A nebulizing catheter constructed and arranged to extend through a flexible tube for bronchial therapy, said nebulizing catheter comprising:
    a catheter sheath defining an interior space and an open tip;
    a nebulizer positioned in said interior space, adjacent said open tip, said nebulizer including a piezoelectric device;
    a one-way air valve positioned within the interior space of said catheter sheath; and a reservoir positioned within the interior space of said catheter sheath between said one-way air valve and said piezoelectric device, said reservoir being constructed and arranged to retain a liquid mixture, wherein said liquid mixture is in flow communication with said piezoelectric device for nebulizing a portion of said liquid mixture into small droplets for use in bronchial therapy.

2. The nebulizing catheter of claim 1 wherein said liquid mixture includes modified cells.

3. The nebulizing catheter of claim 1 wherein said reservoir includes a mesh material.

4. The nebulizing catheter of claim 1 which further includes a porous material which is adjacent said piezoelectric device, said porous material being positioned between said reservoir and said piezoelectric device.

5. The nebulizing catheter of claim 4 wherein said porous material is in communication with said reservoir.

6. The nebulizing catheter of claim 1 wherein said piezoelectric device includes a wave generator.

7. The nebulizing catheter of claim 1 wherein said catheter sheath has an outside diameter of approximately between 3.6 mm and 4.0 mm.

8. The nebulizing catheter of claim 1 wherein said liquid mixture is supplied to said nebulizing catheter by means of a syringe.

9. The nebulizing catheter of claim 1 wherein said liquid mixture is supplied to said nebulizing catheter by means of a tube which is connected to an external supply.

10. The nebulizing catheter of claim 1 wherein said nebulizer includes a porous plug positioned upstream from said piezoelectric device.

11. The nebulizing catheter of claim 10 which further includes a spring, wherein said reservoir is spring-biased by said spring against said porous plug.

12. The nebulizing catheter of claim 1 wherein said nebulizer includes a ceramic sleeve positioned around said piezoelectric device.

13. The nebulizing catheter of claim 12 wherein said ceramic sleeve defines apertures for the passage of air and said liquid mixture.

14. The nebulizing catheter of claim 1 which further includes a holder which is constructed and arranged to assist in the positioning of said piezoelectric device.

15. The nebulizing catheter of claim 1 wherein said piezoelectric device is positioned within a ceramic sleeve and wherein a holder is press-fit into said ceramic sleeve to help maintain the position of said piezoelectric device.

16. The nebulizing catheter of claim 1 wherein said piezoelectric device is an ultrasonic transducer.

17. The nebulizing catheter of claim 1 which further includes a ceramic sleeve and a porous body surrounding said ceramic sleeve.

18. The nebulizing catheter of claim 1 which further includes a ceramic sleeve receiving said piezoelectric device and defining a flow aperture for said liquid mixture.

19. A bronchial therapy device comprising:
 a supply of air;
 a handle connected to said supply of air;
 a bronchoscope including a flexible tube; and
 a nebulizing catheter cooperating with said handle and extending through said flexible tube, said nebulizing catheter comprising:
 a catheter sheath defining an interior space and an open tip;
 a nebulizer positioned in said interior space, adjacent said open tip, said nebulizer including a piezoelectric device;
 a one-way air valve positioned within the interior space of said catheter sheath; and
 a reservoir positioned within the interior space of said catheter sheath between said one-way air valve and said piezoelectric device, said reservoir being constructed and arranged to retain a liquid mixture, wherein said liquid mixture is in flow communication with said piezoelectric device for nebulizing a portion of said liquid mixture into small droplets for use in bronchial therapy.

20. The bronchial therapy device of claim 19 wherein said reservoir includes a mesh material.

21. The bronchial therapy device of claim 19 which further includes a porous material which is adjacent said piezoelectric device, said porous material being positioned between said reservoir and said piezoelectric device.

22. The bronchial therapy device of claim 19 wherein said handle includes a battery which is connected to said piezoelectric device.

23. A nebulizing catheter constructed and arranged to extend through a flexible tube for bronchial therapy, said nebulizing catheter comprising:
 a catheter sheath defining an interior space and an open tip;
 a nebulizer positioned in said interior space, adjacent said open tip, said nebulizer including a piezoelectric device;
 a reservoir positioned within the interior space of said catheter sheath;
 a porous plug positioned within the interior space of said catheter sheath upstream from said piezoelectric device;
 a spring positioned within the interior space of said catheter sheath, wherein said reservoir is spring-biased by said spring against said porous plug; and
 said reservoir being constructed and arranged to retain a liquid mixture, wherein said liquid mixture is in flow communication with said piezoelectric device for nebulizing a portion of said liquid mixture into small droplets for use in bronchial therapy.

24. A method of providing bronchial therapy treatment to a patient site, said method comprising the following steps:
 providing a handle;
 providing a bronchoscope;
 providing a nebulizing catheter which is operatively connected with said handle via said bronchoscope, said nebulizing catheter including a sheath defining an interior space, and a nebulizer with a piezoelectric device;
 providing a reservoir which is positioned within said interior space for retaining a liquid mixture;
 connecting said handle to a supply of air;
 extending a tip of said nebulizing catheter through a flexible tube of said bronchoscope to reach the patient site;
 supplying said nebulizing catheter reservoir with said liquid mixture; and
 energizing said piezoelectric device for converting said liquid mixture into small droplets suitable for treatment.

* * * * *